(12) United States Patent
Henningsen

(10) Patent No.: US 7,226,892 B2
(45) Date of Patent: Jun. 5, 2007

(54) HERBICIDAL COMPOSITION AND USE

(75) Inventor: Kim Carl-Christian Henningsen, Gilleleje (DK)

(73) Assignee: Durga Technologies ApS, Gilleleje (DK)

(*) Notice: Subject to any disclaimer, the term of this patent is extended or adjusted under 35 U.S.C. 154(b) by 214 days.

(21) Appl. No.: 10/947,572

(22) Filed: Sep. 22, 2004

(65) Prior Publication Data

US 2005/0096227 A1   May 5, 2005

Related U.S. Application Data

(63) Continuation-in-part of application No. PCT/DK2004/000067, filed on Feb. 2, 2004.

(60) Provisional application No. 60/505,332, filed on Sep. 23, 2003.

(30) Foreign Application Priority Data

Feb. 3, 2003 (DK) .............................. 2003 00137

(51) Int. Cl.
*A01N 37/00* (2006.01)

(52) U.S. Cl. .................................... 504/320

(58) Field of Classification Search ................ 504/320, 504/116.1, 118
See application file for complete search history.

(56) References Cited

U.S. PATENT DOCUMENTS

| 5,110,348 A | * | 5/1992 | Hopwood | ................... 504/307 |
|---|---|---|---|---|
| 5,705,455 A | | 1/1998 | Lojek | |
| 5,888,938 A | | 3/1999 | Lojek | |
| 2003/0211945 A1 | * | 11/2003 | Lewis | ........................ 504/320 |

FOREIGN PATENT DOCUMENTS

| DE | 40 30 687 A1 | 9/1990 |
|---|---|---|
| EP | 0 604 447 B1 | 8/1992 |
| EP | 0 760 207 A1 | 11/1994 |
| JP | 46-30303 | 8/1962 |
| KR | 8901792 | 5/1989 |
| WO | WO 93/02555 | 8/1992 |
| WO | WO 95/17817 | 12/1994 |
| WO | WO 98/03066 | 7/1997 |
| WO | WO 00/15035 | 8/1999 |
| WO | WO 00/38516 | 12/1999 |
| WO | WO 00/53018 | 3/2000 |

\* cited by examiner

*Primary Examiner*—Johann Richter
*Assistant Examiner*—Ali Soroush
(74) *Attorney, Agent, or Firm*—Michael L. Dunn

(57) ABSTRACT

A herbicidal composition comprises an aqueous solution of a mixture of acetic acid and glycine in a ratio by weight of from 10:1 to 1:1. Preferably, the composition further contains a surfactant. In general, for eradicating herbal vegetation, the aqueous solution has a concentration of acetic acid from 4 to 10% by weight, a concentration of glycine from 1 to 10% by weight and a concentration of surfactant from 0.5 to 5% by weight. The herbicidal composition may conveniently be prepared and shipped as a concentrate adapted to be diluted with water in a ratio by volume from 1:1 to 1:4 before use.

8 Claims, No Drawings

HERBICIDAL COMPOSITION AND USE

CROSS-REFERENCE TO RELATED APPLICATIONS

This application claims priority from U.S. Provisional Application No. 60/505,332 filed Sep. 23, 2003 and a continuation-in-part of International Patent Application PCT/DK2004/000067 filed Feb. 2, 2004, designating the United States and claiming priority from Danish Patent Application PA 2003 00137 filed Feb. 3, 2003.

BACKGROUND OF THE INVENTION

The present invention relates to a herbicidal composition comprising acetic acid and to its use as a contact herbicide on non-woody vegetation.

It is known that acetic acid has a withering down activity as a contact herbicide when sprayed on non-woody vegetation in the form of an aqueous solution. Suggestions to use acetic acid as a herbicide have been made e.g. in DE 4 030 687 (Kast) which describes such use alone or in combination with tensides. Further, a synergistic herbicidal composition consisting essentially of an aqueous solution of acetic acid and citric acid is described in U.S. Pat. No. 5,705,455 and the use of such composition as a herbicide is the subject matter of EP 0 604 447 B1 and U.S. Pat. No. 5,888,938.

BRIEF SUMMARY OF THE INVENTION

The present invention provides a herbicidal composition comprising an aqueous solution of a mixture of acetic acid and glycine in a ratio by weight of from 10:1 to 1:1.

Preferably, the composition also contains a surfactant.

We have found that glycine, which per se has no noticeable herbicidal activity, has an enhancing effect on the herbicidal activity of acetic acid, and that this enhancing effect based on weight is stronger than that of citric acid. Hereby, the herbicide of the invention is effective with a lower total acid content than the prior art mixture of acetic acid and citric acid, i.e. the eco-toxicological load on the environment by use of the herbicide of the invention is lower.

Further, and more important, citric acid has the following risk identification: "Irritates respiratory tract/lungs, irritates eyes, skin irritating", while glycine is not classified as an irritant in any of these respects. Thus, the invention entails an improvement of the human toxicological properties and the work environment as the glycine does not add to the irritating effect that is already involved by the acetic acid and the optional surfactant.

For direct use to spray onto non-woody vegetation the herbicidal composition of the invention generally consists of an aqueous solution having a concentration of acetic acid from 4 to 10% by weight, a concentration of glycine from 1 to 10% by weight and a concentration of surfactant from 0.5 to 5% by weight. More preferably, it consists of an aqueous solution having a concentration of acetic acid from 5 to 8% by weight, a concentration of glycine from 2 to 4% by weight and a concentration of surfactant from 1 to 2% by weight.

The herbicidal composition of the invention may also be in the form of a concentrated aqueous solution adapted to be diluted with water in a ratio from 1:1 to 1:4 before use, said concentrated aqueous solution having a concentration of acetic acid from 8 to 50% by weight, a concentration of glycine from 2 to 50% by weight and a concentration of surfactant from 1 to 25% by weight.

Further, the invention comprises the use of a composition comprising an aqueous solution of a mixture of acetic acid and glycine in a ratio by weight of from 10:1 to 1:1 as a herbicide.

DETAILED DESCRIPTION OF THE INVENTION

Acetic acid with the systematic name ethanoic acid has the chemical formula $CH_3COOH$. It is usually produced by bacterial fermentation of the alcohol ethanol, but may also be produced synthetically. Acetic acid is used in the household and the food industry as vinegar which is essentially a diluted aqueous solution of acetic acid that may also contain various aromas and spices. More concentrated aqueous solutions are used for cleaning purposes and for pH-adjustment in various chemical reactions, and the pure acid is used as an organic solvent. As mentioned above, aqueous solutions of acetic acid have also been used as a contact herbicide for non-woody vegetation.

Glycine with the systematic name 2-aminoethanoic acid has the chemical formula $NH_2CH_2COOH$. It is the most simple of the amino acids making up all peptides and proteins in living organisms. As an amino acid glycine has an amphoteric character and, thus, does not add to the acidity of acetic acid. Its enhancing effect on the herbicidal activity of acetic acid is rather surprising. A possible explanation, which shall not be binding for the invention, is that when taken up by the leaves after treatment glycine decreases the availability of cations by chelation thus increasing the effect of acetic acid by making more binding sites on proteins accessible. This would facilitate denaturation of proteins, leading to non-functional enzymes and, ultimately, cell-death.

The purpose in adding a surfactant to the herbicide of the invention is to secure that the herbicidal solution is dispersed properly on the surface of the herbs and clings to it so that the herbicide can exert its maximum lethal effect on the herbs. Also, the surfactant should aid to keep the glycine in solution and prohibit separation of the herbicide. Suitable surfactants for use in the herbicide of the invention are e.g. is non-ionic surfactants. Preferred surfactants are surfactants comprising an ethoxylated alcohol such as surfactants based on a reaction product of a C8–C15 alcohol with ethylene oxide. Nonionic surfactants based on C10–C13 alcohols are preferred. Examples of preferred surfactants are "Witconol® SN 90" obtained from Witco Corporation, Houston, Tex., U.S.A.; "Berol® EZ-1" obtained from Akzo Nobel Surface Chemistry AB, S-444 85 Stenungsund, Sweden; and "Marlipal® 013/99" obtained from SASOL Germany GmbH, D-45764 Marl, Germany.

It is disclosed in JP46030303 that in glycine polymerisation glycine and a lower aliphatic carboxylic acid such as acetic acid are heated at 100–200° C. However, this reference does not disclose aqueous solutions of glycine and acetic acid or the use thereof.

In some cases, in particular when a surfactant is used that causes foaming of the composition, it may be advantageous to add a small amount of a defoamer, such as "Wacker Silicone Antifoam Emulsion SRE" obtained from Wacker-Chemie GmbH, Munich, Germany, to the herbicidal composition of the invention.

For normal use the concentration of the ingredients in the herbicidal composition of the invention should be such that one complete spraying of herbal vegetation with the herbicidal solution will secure a total withering down of the vegetation within a few days. On the other hand, for environmental reasons the concentration should be kept as low as possible.

The actual concentration necessary for proper effectiveness largely depends on the type and composition of the herbal vegetation. In general, the desired effect may be obtained with a herbicidal composition of the invention wherein the aqueous solution has a concentration of acetic acid from 4 to 10% by weight, and preferably from 5 to 8% by weight, a concentration of glycine from 1 to 10% by weight, and preferably from 2 to 4% by weight, and a concentration of surfactant from 0.5 to 5% by weight, and preferably from 1 to 2% by weight.

If the herbal vegetation is young and does not include resistant herbs like nettles, it could be desirable to use rather low concentrations of the ingredients such as 6% by weight of acetic acid, 2% by weight of glycine and 1.2–2.0% by weight of surfactant or 5% by weight of acetic acid, 3% by weight of glycine and 1.2–2.0% by weight of surfactant or 4% by weight of acetic acid, 4% by weight of glycine and 1.2–2.0% by weight of surfactant. On the other hand, if the vegetation is more established and includes resistant herbs, it may be necessary to use higher concentrations such as 6% by weight of acetic acid, 3% by weight of glycine and 1.6–2.5% by weight of surfactant and/or to recommend repeated treatment after 4–5 days.

It may be convenient to prepare the herbicidal composition of the invention as a concentrate, which can be shipped and sold to professional users and, if allowable, to ordinary consumers and used by them after dilution with water in a ratio by volume from 1:1 to 1:4. This would entail both environmental gains by reducing the amount of packing materials to be removed and economic gains by reducing packing and transport costs. In general, such a concentrate will consist of a concentrated aqueous solution having a concentration of acetic acid from 8 to 50% by weight, a concentration of glycine from 2 to 50% by weight and a concentration of surfactant from 1 to 25% by weight. Normally, a concentrate of the invention will be adapted to be diluted 1:2 or 1:3 by volume.

When a defoamer is added to the herbicidal composition of the invention, it needs only be in a small amount of e.g. 0.01–0.05 g per liter of concentrate adapted to be diluted 1.3, corresponding to 0.0025–0.0125 g per liter in the diluted composition for use.

The invention is described more in detail in the below examples disclosing preferred embodiments of the invention.

EXAMPLES

In the below examples the following ingredients were used

Glycine: 99%, food grade in the form of a white crystalline powder available from Orfa Scansinavia A/S, Jacob Gades Alle 4A, DK-6600 Vejen Denmark.
Acetic Acid: >90% CH3OOH, available from Bie & Berntsen, Sandbaekvej 7, DK-2610 Rødovre, Denmark.
Citric Acid: Citric Acid Monohydrate, (in powder form), available from Bie & Berntsen, Sandbaekvej 7, DK-2610 Rødovre, Denmark.
Water: Tap water.
Method of producing compositions according to the invention:
The liquids stated in the Examples were weighed into a flask in the amounts and order stated and stirred at room temperature until homogeneity after addition of each component.

A common squirt bottle delivering a fine spray was used for spraying the weeds.

Example 1

Glycine Alone—Comparative Example

A solution of 90 g of glycine+15 g of the surfactant "Witconol® SN 90" in 1 L of water was sprayed onto a mixed vegetation of grasses and weeds until the spray liquid dripped from the leaves, corresponding to 0.1 L/m$^2$. No noticeable herbicidal effect was observed.

In the following two experiments the aim is to achieve a total withering down of common grasses not exceeding 10 cm in height and weeds (except nettles) having developed not more than 5 leaves. The compositions are sprayed onto the vegetation until the spray liquid drips from the leaves, corresponding to 0.1 L/m$^2$.

Example 2

Acetic Acid+Citric Acid—Comparative example

A total withering down is only obtained at a total concentration of the acids of 9% by weight, typically composed of 6% acetic acid and 3% citric acid, and further including at least 1.2% by weight of a surfactant.

Thus, with a composition made up of 60 g of acetic acid+30 g of citric acid+12 g of "Witconol® SN 90"+water up to 1 L a total withering down was achieved in about 24 hours.

Example 3

Acetic Acid+Glycine

A total withering down is obtained at a total concentration of the acids of 8% by weight, typically composed of 6% acetic acid and 2% of glycine, and further including at least 1.2% by weight of a surfactant.

Thus, with a composition made up of 60 g of acetic acid+20 g of glycine+12 g of "Witconol® SN 90"+water up to 1 L a total withering down was achieved in about 48 hours, i.e. about 24 hours later than with acetic acid+citric acid.

Example 4

The same result is obtained by use of a composition made up of 50 g of acetic acid+30 g of glycine+12 g of "Witconol® SN 90"+water up to 1 L as well as by use of a composition made up of 40 g of acetic acid+40 g of glycine+12 g of "Witconol® SN 90"+ water up to 1 L.

Example 5

A solution of 60 g of acetic acid+20 g of glycine+12 g of the surfactant "Berol® EZ-1" in 1 L of water was sprayed onto a mixed vegetation of grasses and weeds (except nettles) until the spray liquid dripped from the leaves, corresponding to 0.1 L/m$^2$. A total withering down of the vegetation was achieved in about 48 hours.

Example 6

The same result is obtained when using the surfactant "Marlipal® 013/99" instead of "Berol® EZ-1".

Example 7

A solution of 40 g of acetic acid+40 g of glycine+12 g of the surfactant "Berol® EZ-1" in 1 L of water was sprayed onto a mixed vegetation of grasses and weeds (except nettles) until the spray liquid dripped from the leaves, corresponding to 0.1 L/m². A total withering down of the vegetation was achieved in about 48 hours.

Example 8

The same result is obtained when using the surfactant "Marlipal® 013/99" instead of "Berol® EZ-1".

Example 9

A solution of 50 g of acetic acid+30 g of glycine+12 g of the surfactant "Berol® EZ-1" in 1 L of water was sprayed onto a mixed vegetation of grasses and weeds (except nettles) until the spray liquid dripped from the leaves, corresponding to 0.1 L/m². A total withering down of the vegetation was achieved in about 48 hours.

Example 10

The same result is obtained when using the surfactant "Marlipal® 013/99" instead of "Berol® EZ-1".

Example 11

A solution of 60 g of acetic acid+30 g of glycine+16 g of the surfactant "Berol® EZ-1" in 1 L of water was sprayed onto a mixed vegetation of grasses and weeds (including nettles of a height about 10 cm) until the spray liquid dripped from the leaves, corresponding to 0.1 L/m². A total withering down of the vegetation, including the nettles, was achieved in about 48 hours.

Example 12

The same result is obtained when using the surfactant "Marlipal® 013/99" instead of "Berol® EZ-1".

What is claimed is:

1. A herbicidal composition comprising an aqueous solution of a mixture of acetic acid and glycine in a ratio by weight of from 10:1 to 1:1.

2. A herbicidal composition according to claim 1 further containing a surfactant.

3. A herbicidal composition according to claim 2 wherein the surfactant is a non-ionic surfactant.

4. A herbicidal composition according to claim 3 wherein the surfactant comprises an ethoxylated alcohol.

5. A herbicidal composition according to claim 2 wherein the aqueous solution has a concentration of acetic acid of from about 4 to about 10% by weight, a concentration of glycine from about 1 to about 10% by weight and a concentration of surfactant from about 0.5 to about 5% by weight.

6. A herbicidal composition according to claim 5 wherein the aqueous solution has a concentration of acetic acid from 5 to 8% by weight, a concentration of glycine from 2 to 4% by weight and a concentration of surfactant from 1 to 3% by weight.

7. A herbicidal composition according to claim 1 comprising a concentrated aqueous solution adapted to be diluted with water in a ratio by volume from 1:1 to 1:4 before use, said concentrated aqueous solution having a concentration of acetic acid from 8 to 50% by weight, a concentration of glycine from 2 to 50% by weight and a concentration of surfactant from 1 to 25% by weight.

8. A method for controlling vegetation comprising applying a composition comprising an aqueous solution of a mixture of acetic acid and glycine in a ratio by weight of from 10:1 to 1:1 to the vegetation as a herbicide.

* * * * *